United States Patent [19]

Scheib et al.

[11] Patent Number: 5,457,202
[45] Date of Patent: Oct. 10, 1995

[54] RESOLUTION OF 5-METHYLTETRAHYDROFOLIC ACID

[75] Inventors: Klaus Scheib, Schauernheim; Peter Klein, Birkenheide, both of Germany; Robert Carter, Basel, Switzerland

[73] Assignee: Knoll Aktiengesellschaft, Ludwigshafen, Germany

[21] Appl. No.: 232,267

[22] PCT Filed: Nov. 3, 1992

[86] PCT No.: PCT/EP92/02515

§ 371 Date: May 6, 1994

§ 102(e) Date: May 6, 1994

[87] PCT Pub. No.: WO93/10118

PCT Pub. Date: May 27, 1993

[30] Foreign Application Priority Data

Nov. 11, 1991 [DE] Germany .......................... 41 36 921.1

[51] Int. Cl.$^6$ .................................................. C07D 475/04
[52] U.S. Cl. ............................................ 544/258; 548/566
[58] Field of Search .................................................. 544/258

[56] References Cited

U.S. PATENT DOCUMENTS

| | | | |
|---|---|---|---|
| 5,006,655 | 4/1991 | Müller et al. | 544/258 |
| 5,010,194 | 4/1991 | Müller et al. | 544/258 |
| 5,134,235 | 7/1992 | Mueller et al. | 544/258 |
| 5,194,611 | 3/1993 | Marazza et al. | 544/258 |
| 5,334,535 | 8/1994 | Schlingmann et al. | 435/280 |
| 5,350,850 | 9/1994 | Vecchi | 544/258 |

FOREIGN PATENT DOCUMENTS

| | | |
|---|---|---|
| 266042 | 4/1988 | European Pat. Off. . |
| 293029 | 11/1988 | European Pat. Off. . |
| 367902 | 5/1990 | European Pat. Off. . |
| 348641 | 1/1991 | European Pat. Off. . |
| 432441 | 6/1991 | European Pat. Off. . |
| 455013 | 12/1991 | European Pat. Off. . |
| 495204 | 7/1992 | European Pat. Off. . |
| WO91/13890 | 9/1991 | WIPO . |
| 93/10118 | 5/1993 | WIPO .................................. 544/258 |

OTHER PUBLICATIONS

Clinical Science and Molecular Medicine, vol. 45, 1973, Weir et al. The Absorption of the Diastereoisomers of 5-Methyltetrahydropteroylglutamate.
Japanese Abst. JA 12 586/68 (1968).

*Primary Examiner*—Donald G. Daus
*Attorney, Agent, or Firm*—Keil & Weinkauf

[57] ABSTRACT

A process for preparing (6S)-5-methyltetrahydrofolic acid by resolution of racemic (6R,S)-5-methyltetrahydrofolic acid using a base, wherein the base is N-ethyl-2-aminomethylpyrrolidine or its optical isomers.

1 Claim, No Drawings

RESOLUTION OF 5-METHYLTETRAHYDROFOLIC ACID

This application is a Section 371 filing of PCT/EP92/02515 filed Nov. 3, 1992.

The present invention relates to a process for the resolution of (6R,S)-5-methyltetrahydrofolic acid of the formula

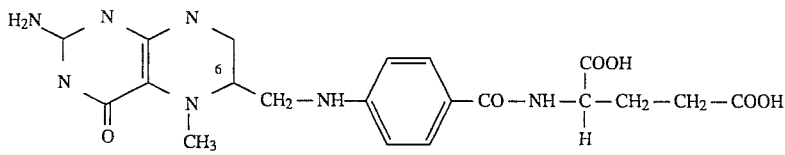

This acid is also called N-(5-methyl)-(6R,S)-5,6,7,8-tetrahydropteroyl)-L-glutamic acid. It is prepared from folic acid by methylation and hydrogenation, and resolution into its diastereomers by chemical means is regarded as impossible (Clinicel Science and Molecular Medicine 45 (1973) 625–631).

5-Methyltetrahydrofolic acid has importance as a drug ingredient for 2 main indication areas:

a) in oncology as concomitant therapy with methotrexate and 5-fluorouracil treatment and
b) in the treatment of folic acid deficiency anemia associated with pregnancy, antibiotic therapy etc.

Calcium 5-methyltetrahydrofolate is the only folic acid derivative on the market which is able directly to penetrate the blood/brain barrier without further metabolism.

Naturally occurring 5-methyltetrahydrofolic acid is solely in the S form; the R form is biochemically inactive and is excreted through the kidney.

We have now found a process which can be used to resolve the acid into its diastereomers.

The present invention relates to a process for preparing (6S)-5-methyltetrahydrofolic acid by resolution of racemic (6R,S)-5-methyltetrahydrofolic acid using a base, wherein the base is N-ethyl-2-aminomethylpyrrolidine or its optical isomers.

The process is carried out by taking up the acid or a water-soluble salt thereof in water and adding a solution of N-ethyl-2-aminomethylpyrrolidine or an optical isomer of this compound in water. This results in precipitation of the salt of the acid with the pyrrolidine derivative. Heating the reaction mixture to 40–90, preferably 60°–80° C. results in the salt of the 6S-acid dissolving, and it can thus be separated from the salt of the 6R-acid. The salt of the 6S-acid precipitates again on cooling the solution.

Suspension of the latter in water and addition of sodium hydroxide solution results in the sodium salt which can be converted with, for example, an alkaline earth metal hydroxide or chloride into an alkaline earth metal salt such as the calcium salt.

The N-ethyl-2-aminomethylpyrrolidine can, as already mentioned, be used either as racemate or in the form of its optical isomers for the racemate resolution. The (−)-amine is most suitable.

EXAMPLE 1

51 g of N-ethyl-2-aminomethylpyrrolidine were added to 92 g of (6R,S)-5-methyltetrahydrofolic acid in 600 ml of water. The reaction mixture was heated to 60° C. and stirred vigorously at this temperature for 1 h. After filtration, the filtrate was cooled to 20° C., and the crystals (36 g, $[\alpha]_D^{20}$: +24.5° (c=1 in 0.6% Trilon B)) were filtered off with suction.

Suspension of the resulting salt in 220 ml of water, addition of 15 g of calcium chloride and heating to 35° C. resulted, after cooling to 17° C., in 30 g of (6S)-calcium tetrahydrofolate [sic]×5 $H_2O$, $[\alpha]_D^{20}$: +34.5° (C=1 in 0.6% ®Trilon B). The optical purity of the product was more than 99%.

EXAMPLE 2

117.5 g of calcium (6R,S)-5-methyltetrahydrofolate were suspended in 100 ml of water under nitrogen, and 58.45 g of ethylenediaminetetraacetic acid were added to form the calcium complex. After addition of 51.2 g of (−)-N-ethyl-2-aminomethylpyrrolidine, the mixture was heated to 85° C. After cooling to 60° C., the sparingly soluble 6R-salt was filtered off with suction. The mother liquor was cooled to 20° C., and the resulting crystals were filtered off with suction and washed with water. 46.2 g of pure pyrrolidine salt of (6S)-5-methyltetrahydrofolic acid were obtained.

EXAMPLE 3

Example 2 was repeated but (+)- was used in place of (−)-N-ethyl-2-aminomethylpyrrolidine. 25 g of pyrrolidine salt of (6S)-5-methyltetrahydrofolic acid were obtained.

EXAMPLE 4

Example 2 was repeated but (±)- was used in place of (-)-N-ethyl-2-aminomethylpyrrolidine. 28 g of pyrrolidine salt of (6S)-5-methyltetrahydrofolic acid were obtained.

We claim:

1. A process for preparing (6S)-5-methyltetrahydrofolic acid by resolution of racemic (6R,S)-5-methyltetrahydrofolic acid using a base, wherein the base is N-ethyl-2-aminomethylpyrrolidine or its optical isomers.

* * * * *